United States Patent [19]

Fang

[11] Patent Number: 5,045,364
[45] Date of Patent: Sep. 3, 1991

[54] NONLINEAR OPTICAL DEVICES AND METHODS

[75] Inventor: Treliant Fang, Lawrenceville, N.J.

[73] Assignee: AT&T Bell Laboratories, Murray Hill, N.J.

[21] Appl. No.: 525,947

[22] Filed: May 18, 1990

[51] Int. Cl.⁵ .............................................. B32B 9/04
[52] U.S. Cl. .................................... 428/411.1; 372/20; 372/29; 427/12; 427/44; 427/53.1; 427/58; 427/162; 427/331; 359/321; 359/328; 385/16; 385/42; 385/122
[58] Field of Search .................... 427/44, 12, 53.1, 58, 427/162, 33.1; 428/411.1; 307/425, 427; 350/96.14, 96.34; 372/20, 29

[56] References Cited

U.S. PATENT DOCUMENTS

4,859,876 8/1989 Dirk et al. .......................... 307/425

*Primary Examiner*—Bernard Pianalto
*Attorney, Agent, or Firm*—R. B. Anderson

[57] ABSTRACT

Optically nonlinear device elements such as directional couplers, switches, frequency stabilizers, optical parameters devices and modulators use as an optically nonlinear element a cross-linked triazine polymer containing a covalently bonded optically nonlinear dye moiety. A specific cross-linked triazine with this dye moiety may be made by cyclotrimerizing a p-(N,N-bis(4'-cyanatobenzyl)amino-p'-(2,2-dicyanovinyl)azobenzene monomer. During polycyclotrimerization or cure, the element is subjected to a poling voltage which aligns the dipoles of the dye moiety to give a large useful nonlinear susceptibility.

7 Claims, 5 Drawing Sheets

NONLINEAR OPTICAL DEVICES AND METHODS

TECHNICAL FIELD

This invention relates to nonlinear optical devices such as electrooptic modulators and switches, frequency converters, data processors, optical parametric oscillators and amplifiers, and optically nonlinear materials useful in such devices.

BACKGROUND OF THE INVENTION

Optical transmission systems have come into widespread use primarily because of the ability of optical fibers to transmit much greater quantities of information than other comparable transmission media. Processing of such information normally requires that the information be converted to an electronic form. Thus, it has long been realized that if such functions as modulation, switching, mixing, data processing and the like could be performed directly on lightwaves, optical communications systems could be made to be much more efficient. It is also known that optically nonlinear materials can be used to make electrooptical modulators, switches, optical parametric devices and other devices for operating directly on lightwaves. Lithium niobate is the most commonly used nonlinear medium, although certain organic crystalline materials have also been proposed.

The U.S. Pat. No. 4,859,876, of Dirk et al., granted Aug. 22, 1989, hereby incorporated herein by reference, describes a nonlinear element comprising a glassy polymer containing an optically nonlinear organic moiety. The nonlinearity results from electric poling which aligns permanently dipoles within the polymer. The glassy polymer that was principally described was polymethylmethacrylate (PMMA), while other acrylate based polymers were also mentioned. The Dirk et al. patent represents a significant advance of the state of the art since polymers such as PMMA can be applied as a film to a substrate and their properties controlled much more easily and accurately than crystalline substances. The PMMA films constituting the heart of the various electrooptic devices may range from only about one micron to about two hundred microns in thickness.

A problem with the nonlinear devices of Dirk et al. is that their nonlinear susceptibility tends to deteriorate over time, particularly when subjected to high temperatures on the order of or exceeding 80° C. Such lower susceptibilities generally mean that the devices perform the functions for which they were intended with less efficiency than would otherwise be the case. As a consequence, systems which use these devices may required special cooling apparatus to keep the devices from reaching elevated temperatures and other design precautions may be required to compensate for a deterioration of optical properties with time.

SUMMARY OF THE INVENTION

In accordance with the invention, an optically nonlinear element comprises cross-linked triazine polymer containing a covalently bonded optically nonlinear dye moiety. Cured triazine strongly stabilizes this dye moiety, and such stabilization continues over time and under conditions of high temperature. This stability also characterizes the dipole alignment needed for high nonlinear susceptibility. The triazine offers the advantages of the materials described in the Dirk et al. patent, such as ease of use in a thin film form, and yet is inherently thermally stable. As will be described in detail, triazine polymer can be made with a dicyanovinylazo moiety that is capable of maintaining a large nonlinear susceptability while being transparent over a useful optical wavelength of about 0.8 to about 2.0 microns. A specific cross-linked triazine with this dye moiety may be made by cyclotrimerizing a p-(N,N-bis(4'-cyanatobenzyl)amino)-p'-(2,2dicyanovinyl)azobenzene monomer. During the cyclotrimerization or cure, the element is subjected to a poling voltage which aligns the dipoles of the dye moiety to give a large useful nonlinear susceptibility.

These and other objects, features and advantages of the invention will be better understood from a consideration of the following detailed description taken in conjunction with the accompany drawing.

DETAILED DESCRIPTION

The devices described herein operate directly on light waves and illustrate different device functions. These devices make use of a polymer, specifically, triazine, having within it a constituent that has a finite nonlinear optical susceptibility. This nonlinear optical characteristic is imposed by the known process of electric poling, in which an electric field is applied to the material to align dipoles of constituent molecules permanently in generally the same direction during cure. The devices of FIGS. 1-5 demonstrate various ways in which the nonlinear optical susceptibility of such a nonlinear polymeric element can be exploited. In all of these devices, it is intended that the nonlinear material be substantially transparent at the optical wavelength of operation; that is, its attenuation at such wavelength is sufficiently low so as to allow for a commercially operable and feasible device.

Figure 1:
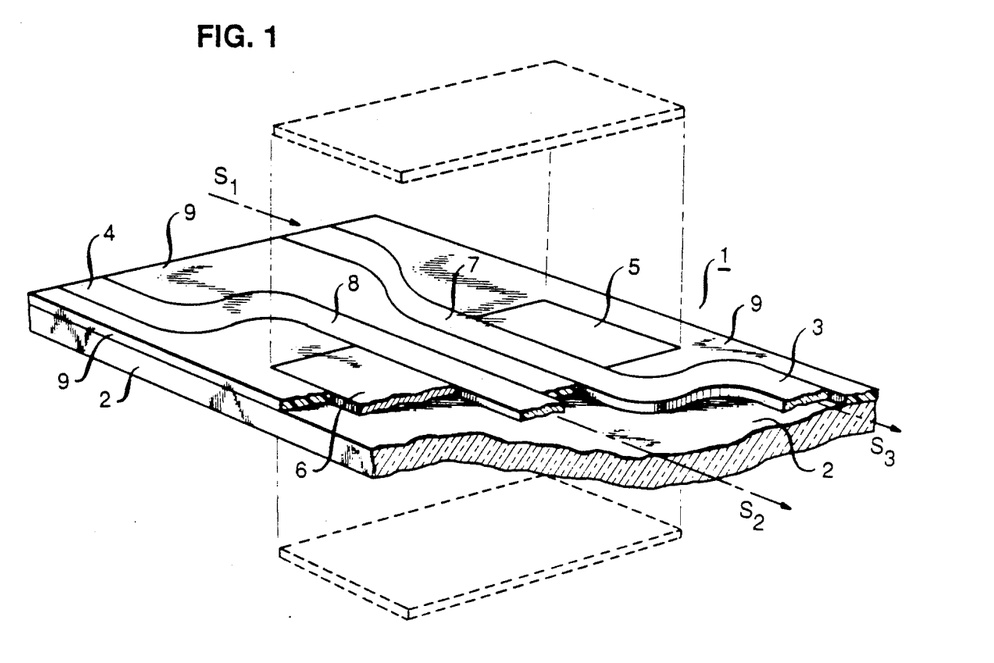
FIG. 1 is a schematic perspective view of an electro-optical directional coupler or switch in accordance with an illustrative embodiment of the invention.

Referring to FIG. 1, there is shown schematically an electrooptic directional coupler or switch 1. The coupler comprises a substrate 2, a pair of spaced channel waveguides 3 and 4 on one surface of the substrate, and a pair of electrodes 5 and 6, one electrode associated with and contiguous to each of the channel waveguides. At a central regions 7 and 8 of the waveguides 3 and 4, respectively, the waveguides are parallel to each other and the spacing between them is small, typically from five to twenty microns. The electrodes 5 and 6 are positioned adjacent the waveguides in this narrowly spaced region so as to maximize the electric field developed across the waveguides upon application of a voltage to the electrodes. Alternatively, as shown by the dotted lines, one may employ top and bottom electrodes on opposite sides of the waveguides to enhance the field for a given applied voltage.

The waveguides 3 and 4 are made of a triazine material exhibiting a nonlinear optical susceptibility in response to an applied electric field. Light, preferably from a laser, is directed into one end of waveguide 3 as designated by $S_1$. In the absence of any applied field, the electromagnetic field associated with the light extends beyond the confines of waveguide 3 and penetrates waveguide 4 in region 8 of that waveguide. If the length of the portions 7 and 8 are properly selected, the light will essentially be emitted from waveguide 4 as shown by $S_2$. There is thus a complete transfer of the light from one waveguide to the other. By applying an appropriate voltage by means of the electrodes, the nonlinear response of the waveguide material to the electric field can produce a slight change in the transmission characteristic of the waveguide. When properly adjusted, this voltage or electric field will prevent the transfer of light from one waveguide to the other and the light will be transmitted directly through waveguide 3 so as to be emitted as shown by $S_3$. The nonlinear optical susceptibility is often designated by $\chi$, whose value is a designation of the efficiency of the element; that is, the higher the value of $\chi$ the greater the response to an applied electric field. When an optically nonlinear material responds to a voltage or an electric field in this manner, it is often referred to as electrooptic material.

Figure 2:
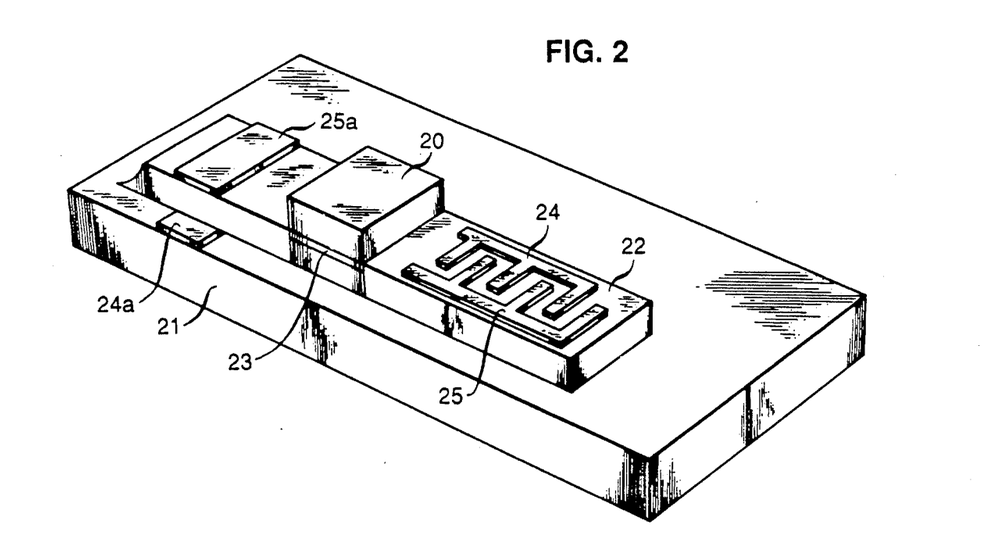
FIG. 2 is a schematic perspective view of an integrated solid state laser tuner and frequency stabilizer, within which the invention is used.

FIG. 2 shows an integrated laser tuner and frequency stabilizer using the triazine nonlinear or electrooptic medium described herein. A junction or injection laser 20 is devised such as to have a light emitting junction 23 which is contiguous to a thin electrooptic film. The film 22 may be provided with opposing electrodes 24 and 25 as shown on one side of the laser, or by electrodes 24a and 25a as shown on the other side of the laser. Either electrode configuration can be used to excite an optically nonlinear response in the nonlinear film 22. The electrooptical effect of the film under properly applied fields results in a useful tunable filter function, or as a frequency stabilizer of the laser output.

Figure 3:
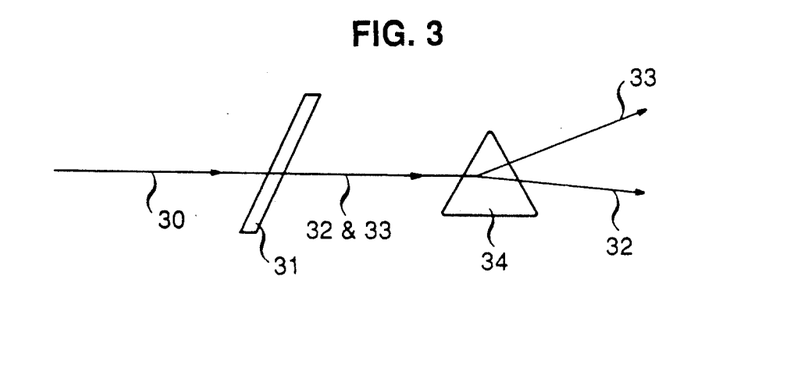
FIG. 3 is a diagrammatic representation of a device for generating second harmonic frequencies, within which the invention is used.

FIG. 3 shows the triazine optically nonlinear medium used in an optical parametric device for second harmonic frequency generation. Here an incident light beam 30 at a frequency f impinges on the optically nonlinear film 31. Due to the nonlinear optical properties, two colinear beams 32 and 33 are emitted, one at the same frequency f and one at twice the original frequency 2f. The emerging colinear beams 32 and 33 may be directed through a prism 34 which spatially separates them into separate beams 32 and 33. The beam of frequency 2f may be used independently of the other beam if for any of various reasons a higher 2f frequency is desirable. This embodiment demonstrates that an applied electric field is not always required for the nonlinear optical element to preform a useful function.

Figure 4:
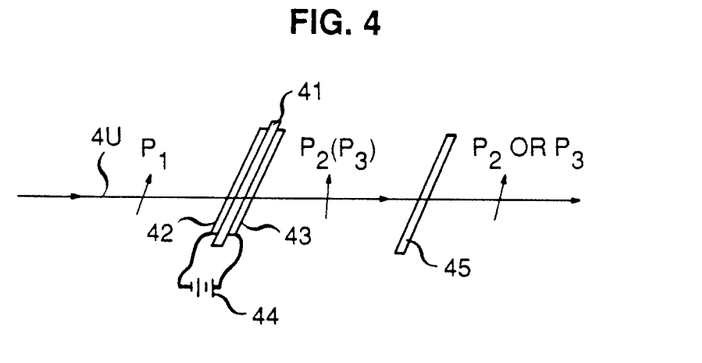
FIG. 4 is a diagrammatic representation of an electrooptic phase/intensity modulator within which the invention is used.

FIG. 4 shows the use of a triazine nonlinear polymer film in an electrooptical phase/intensity modulator. Here, incident light 40 having a polarization $P_1$ is passed through a nonlinear film 41, which is provided with transparent electrodes 42 and 43 on opposite surfaces. Upon passing through the film, the natural birefringence of the optically nonlinear film causes a change of polarization of the light to $P_2$. When a voltage is applied to the film by means of a voltage source 44, the electric field applied to the film changes its optical properties. The nonlinear response causes a change in the film's index of refraction, thereby altering its birefringence and this, in turn, causes the emitted light to have yet a different polarization designated as $P_3$. Thus, a polarization modulation between the values $P_2$ and $P_3$ can be achieved through periodic applications of the voltage to the film 41. An intensity modulation can optionally be obtained by placing a polarizer 45 at the output path of the beam which is oriented to allow the passage of either $P_2$ or $P_3$, but not both. It should be noted that the nonlinear optical film of both devices of FIGS. 3 and 4 are preferably deposited on a transparent substrate.

Figure 5:
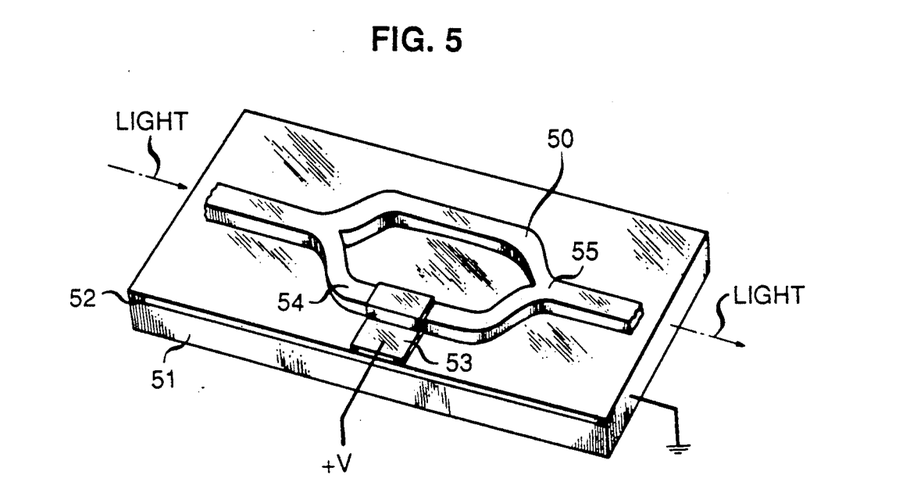
FIG. 5 is a perspective schematic view of an electro-optical guided wave intensity modulator within which the invention is used.

FIG. 5 shows a guided wave electrooptic intensity modulator employing a triazine nonlinear optical layer 50. The film 50 is formed on a conductive substrate 51 having an insulative coating 52. The film is formed as an interferometric waveguide structure with an electrode 53 placed on one arm 54 of the interferometer. As voltages are applied to arm 54 by electrode 53, an electric field is produced in arm 54 of the interferometer. This field changes the index of refraction of the material and results in an effective change of the optical path length in arm 54 of the interferometer relative to the other arm. This in turn produces either constructive or destructive interference of light at a recombination point 55. As the voltage is modulated so as to alternate between constructive and destructive conditions, the output intensity varies between maximum and minimum values as well.

The nonlinear optical medium used in all of the devices of FIGS. 1–5 and other electrooptic and optical parametric devices that may be made in accordance with the invention, comprises cross-linked triazine containing a covalently bonded optically nonlinear dye moiety. In accordance with one feature of the invention, the dye moiety may be dicyanovinylazo dye, which is substantially transparent to light having wavelengths between 0.8 and 2.0 microns and, accordingly, the light with which such devices are used should be of a corresponding wavelength. The dipoles of the triazine molecules are aligned by applying a poling voltage during cure (i.e., during, cross-linking), as will be explained more fully later. A detailed method that I have used in the laboratory for making triazine with a dicyanovinylazo moiety will now be discussed.

Figure 6:
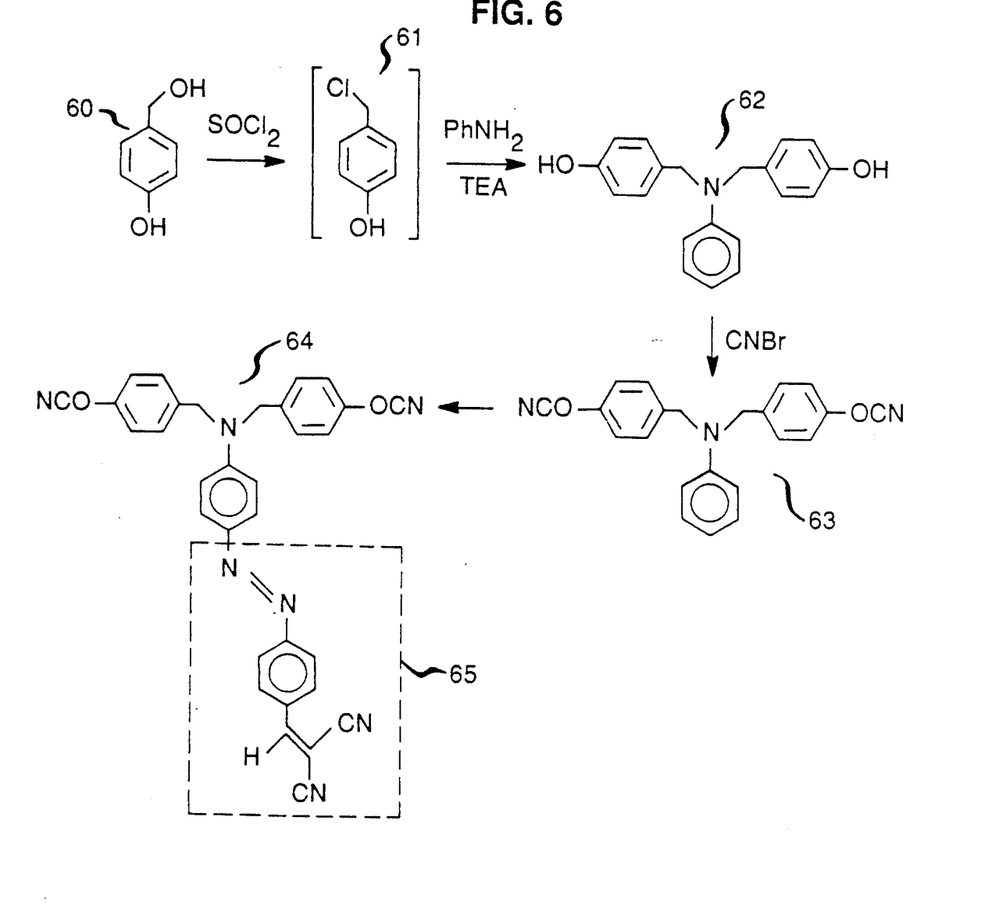
FIG. 6 is a diagrammatic illustration of a method for making a synthetic monomer in accordance with one feature of the invention.
Figure 7:
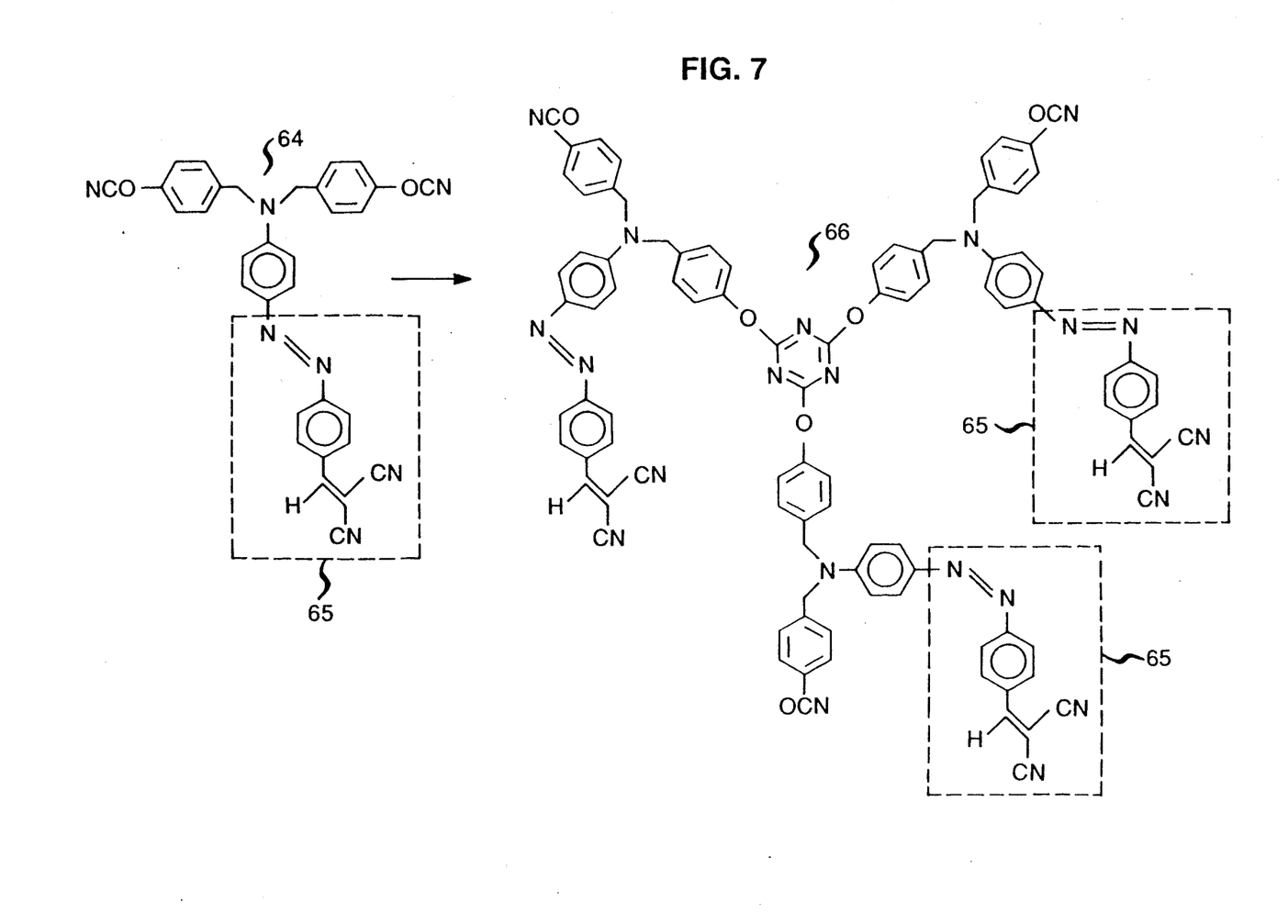
FIG. 7 is a diagrammatic illustration of a method for making triazine polymer from the monomer of FIG. 6.

FIG. 6 summarizes a method for making a synthetic monomer in accordance with the invention while FIG. 7 shows the method for making triazine oligomers from the synthesized monomer; the final polymer results from curing the oligomers. Referring to FIG. 6, 60 refers to a starting material; 7.0 grams of thionyl chloride ($SOCl_2$) was added drop by drop into a solution of material 60 in sixty milliliters of $CH_3CN$. This yielded an intermediate 61 which was separated from a gummy residue by draining from a separatory funnel. The intermediate 61 was added over ten minutes into a well stirred solution at room temperature of 2.36 grams of aniline ($PhNH_2$) in twelve grams of triethylamine (TEA). After filtering off triethylammonium hydrochloride, the solution was concentrated to yield a syrup of the intermediate compound shown in FIG. 6 as 62, which may be designated as bis(4-hydroxybenzyl)aniline. Seven grams of the intermediate 62 was dissolved in fifteen milliliters of acetone and the solution cooled in a xylene liquid nitrogen bath to −15° C. To this was added a solution of cyanogen bromide (CNBr) in acetone (3.0 grams CNBr in seven milliliters of acetone). This was followed by the addition by drops of four grams of triethylamine. The temperature was maintained at about −10° C. for fifteen minutes and then warmed to room temperature in one hour. This yielded the intermediate 63 which may be designated as bis(4-cyanatobenzyl) aniline.

Seven hundred milligrams of intermediate 63 were dissolved in twenty milliliters of acetone. To this was added four drops of acetic acid and a solution of one thousand eighty milligrams of diazonium salt (4-(2,2,-dicyanovinyl)benzene diazonium hexafluorophosphate) in twelve milliliters of acetone. It should be noted that the diazonium salt eventually constitutes the dye moiety of the final polymer. The mixture was stirred in a nitrogen atmosphere for eighteen hours at room temperature and then heated at 44° C. for one hour. The mixture was then mixed with fifty milliliters of equal parts of acetone and water and the precipitate collected and washed with water until neutral. When dried, this yielded 1.15 grams of intermediate 64, a monomer which may be designated as p-(N,N-bis(4'-cyanatobenzyl) amino)-p'-(2,2-dicyanovinyl)azobenzene.

Referring to FIG. 7, the monomer 64 (100 milligrams) was next dissolved in a solvent such as methylethylketone (MEK) or γ-butryrolactone (500 milligrams). The γ-butyrolacetone is preferred. To this solution was added a metal complex catalyst at a concentration of between 0.1 to five percent by weight of the monomer, preferably 08. to 2.0 percent. Typical catalysts are copper benzoylacetonate (CBA), zinc benzoylacetonate, and copper or zinc naththenate, although CBA is preferred. This solution was then heated in a sealed tube at 150° C. for thirty minutes to initiate cyclotrimerization. The resulting oligomer solution is appropriate for coating as by spin-coating on a substrate such as an aluminized wafer. The coating is next polymerized or, more specifically, polycyclotrimerized, by heating at a temperature of between 100° and 170° C., preferably between 130° and 160° C. The temperature is preferably raised quickly to 100° C., and thereafter raised at about two degrees per minute to the final temperature, and is held at the final temperature for about one-half hour.

The oligomer 66 contains a dicyanovinylazo dye moiety 65 which may be poled to impart a nonlinear optical susceptibility. During the cure, an electric field typically of $1 \times 10^6$ volts per centimeter or more is applied to the coating so as to pole the dye moiety. The electric field may be applied between parallel electrode plates, or alternatively may be applied by corona poling as is known in the art.

During cure, the solution was polycyclotrimerized to yield a cross-linked triazine polymer which has been poled to be optically nonlinear. As is known, cross-linked triazine extends in three dimensions and therefore differs from polymers such as PMMA which extends in only two dimensions. The geometry resulting from three-dimensional cross-linking is believed to confine the poled dye moieties 65 more strongly than would be the case with two-dimensional polymers. As a consequence, over time and under conditions of relatively high temperature, the dye moieties 65 remain firmly confined within the triazine polymeric structure.

Figure 8:
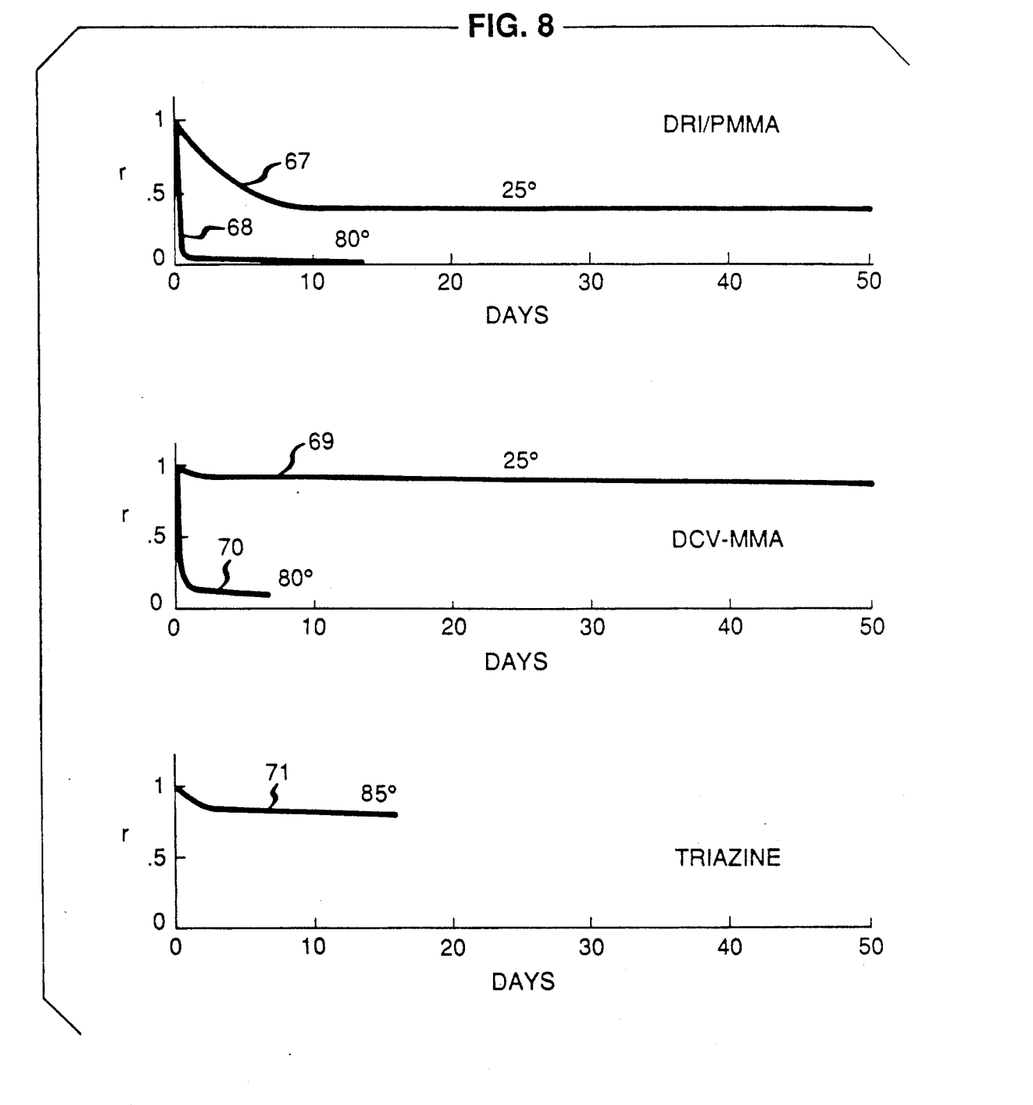
FIG. 8 is a graph comparing the thermal stability of two optically nonlinear materials of the prior art with that of a triazine material made in accordance with the invention.

This advantage has been verified experimentally in tests, the results of which are summarized in FIG. 8 FIG. 8 shows the variation of r for three different materials as a function of time in days, where r is the ratio of the electrooptical coefficient of the poled film to the original electrooptic coefficient. Thus, if there is no change with time, r will remain one. The electrooptic coefficient is a function of both the optical susceptibility (in this case, the second order optical susceptibility) and the density of nonlinear moieties. Thus, a decay of r generally indicates a decay in number of effective nonlinear moieties. Curve 67 shows the change of electrooptic coefficient with respect to time of the material discussed in the Dirk et al. patent, namely, disperse red dye 1 dissolved in polymethylmethacrylate (DR1/PMMA). At 25° C., room temperature, the curve 67 shows a reduction of electrooptic coefficient after ten days to a value of less than half the original value. Curve 68 shows that at 80° C. there is a precipitate drop to virtually zero, which indicates that the material could not practically be used at that temperature. Curve 69 is an example of a covalently bonded nonlinear dye molecule in a glassy polymer host as described in general in the Dirk et al. patent, the material being dicyanovinylazobenzene-methylmethacrylate (DCV-MMA). Curve 69 shows that there is some deterioration with time at 25° C. Curve 70 again shows a precipitate drop in electrooptic coefficient at 80° C. and thereafter a continued deterioration with time.

Curve 71 shows the change of electrooptical coefficient of triazine at 85° C. one can see that even at this high temperature, there is only a modest deterioration and that, after ten days, the second order optical susceptibility is about eight-tenths of its original value. The original measured value of the second order optical susceptibility $\chi^{(2)}$ was equal to about $75 \times 10^{-9}$ esu (electrostatic units). This demonstrates that triazine is practical for use as a nonlinear element in the various devices of FIGS. 1–5, in environments that may consistently be heated to temperatures as high as 85° C., and that such reliability has an extended lifetime.

The triazine oligomer solution that we have described can be coated on any of various substrates using any of various techniques well known in the art. After coating, the solvent is removed during the heat and cure process. Multiple coatings can be made, but it is believed that most useful device coatings will be in the thickness range of one micron to two hundred microns. Any of various substrates can be used and a poling conductor may be provided on one surface of the substrate.

Figure 9:
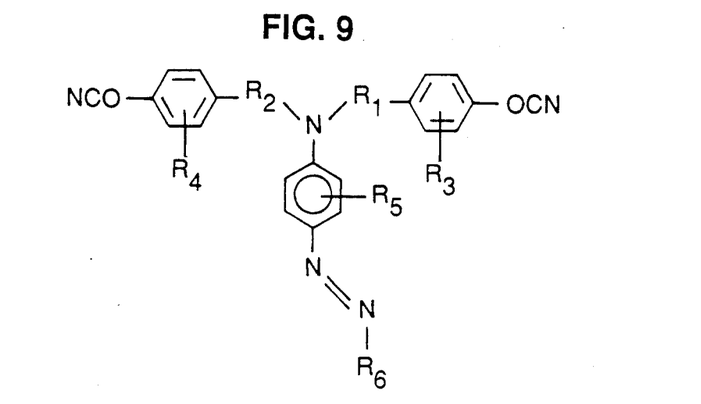
FIG. 9 is a diagrammatic illustration of a generalized monomer that can be used for making triazine in accordance with one aspect of the invention.

The monomer 64 of FIGS. 6 and 7 from which the triazine molecule is made should be considered as only one example of a suitable triazine precursor. FIG. 9 shows a generalized formula for triazine precursors that could be used. In FIG. 9, R1 and R2 may be $(CH_2)n$ or which may also be designated as 2-(4'-methylenephenylene)propylidenyl, where n is an integer from zero to ten. R3 and R4 may be hydrogen, alkyl, alkenyl, alkoxy, or aryloxy. R5 may be hydrogen, alkyl or alkoxy. R6 may be p-(2,2-dicyanovinyl)phenyl, p-(1,2,2-tricyanovinyl)phenyl, 5-(2.2-dicyanovinyl)thiazolyl, 5-(1,2,2-tricyanovinyl)thiazolyl, 4-chloro-5-(2,2-dicyanovinyl)thiazolyl, 4-chloro-5-(1,2,2-tricyanovinyl)thiazolyl, or 5-nitrothiazolyl.

The foregoing has shown in detail how cross-linked triazine containing an optically nonlinear dye moiety can be made and used in any of various useful devices. The second order susceptibility is competitive to that of materials described in the prior art, even at elevated temperatures, but it may have useful susceptibilities at the third or higher orders as well. Various other methods for making triazine with such dye moiety may be made by those skilled in the art without departing from the general teachings hereof. Devices other than those explicitly described for making use of triazine as the optically nonlinear element may likewise be made by those skilled in the art. Various other embodiments and modifications of the invention may be made without departing from the spirit and scope of the invention.

I claim:

1. A method for making a nonlinear optical device comprising the steps of:

synthesizing a monomer containing a dye moiety;

cyclotrimerizing the monomer in solution form to make a triazine oligomer solution;

spreading the oligomer solution on a substrate;

polycyclotrimerizing the oligomer in the presence of an electric field of sufficient intensity to align dipoles of the dye moiety, thereby to form an optically nonlinear film of cross-linked triazine on the substrate;

and defining an optical input means at one part of the triazine film and an optical output means at another part of the triazine film.

2. The method of claim 1 to wherein:
the monomer is of the form shown in FIG. 9 hereof.

3. The method of claim 2 wherein:
the monomer is p-(N,N-bis(4'-cyananatobenzyl)amino)-p'-(2,2dicyanovinyl)azobenzene.

4. The method of claim 3 wherein:
the monomer is made by the process of FIG. 6 hereof.

5. The method of claim 1 wherein:
the dye moiety is a dicyanovinylazo moiety.

6. The method of claim 1 wherein:
the spreading step comprises spinning the oligomer solution to a thickness of one micron to two hundred microns.

7. A nonlinear optical device made by the method of claim 1.

* * * * *

UNITED STATES PATENT AND TRADEMARK OFFICE
CERTIFICATE OF CORRECTION

PATENT NO. : 5,045,364

DATED : September 3, 1991

INVENTOR(S) : T. Fang

It is certified that error appears in the above—identified patent and that said Letters Patent is hereby corrected as shown below:

Title Page, In the Abstract, lines 2-3
  after "optical" change "parameters" to --parametric--;

Column 1, line 51
  after "may" change "required" to --require--;

Column 2, lines 2-3
  after "nonlinear" change "susceptability" to --susceptibility--;

Column 4, line 48
  after "between" change "08." to --0.8--;

Column 4, line 52
  after second occurrence of "during" delete the comma;

Column 5, line 38
  after "preferably" change "08." to --0.8--;

Column 5, line 40
  after "zinc" change "naththenate" to --naphthenate;

Column 6, line 66
  change "$\{CH_2\text{—}\langle\bigcirc\rangle\text{—}C(Me)\}$" to --$\{CH_2\text{—}\langle O\rangle\text{—}C(Me)_2\}_{\overline{n}}$--.

Column 8, line 13
  after "1" delete "to".

Signed and Sealed this

Twelfth Day of January, 1993

Attest:

DOUGLAS B. COMER

*Attesting Officer*   Acting Commissioner of Patents and Trademarks